(12) United States Patent
Koskela et al.

(10) Patent No.: US 11,980,439 B2
(45) Date of Patent: May 14, 2024

(54) OPTICAL SENSOR SYSTEM OF A WEARABLE DEVICE, A METHOD FOR CONTROLLING OPERATION OF AN OPTICAL SENSOR SYSTEM AND CORRESPONDING COMPUTER PROGRAM PRODUCT

(71) Applicant: Oura Health Oy, Oulu (FI)

(72) Inventors: Markku Koskela, Oulu (FI); Tero Vallius, Oulu (FI)

(73) Assignee: Oura Health Oy, Oulu (FI)

( * ) Notice: Subject to any disclaimer, the term of this patent is extended or adjusted under 35 U.S.C. 154(b) by 771 days.

(21) Appl. No.: 17/055,616

(22) PCT Filed: May 27, 2019

(86) PCT No.: PCT/FI2019/050407
§ 371 (c)(1),
(2) Date: Nov. 16, 2020

(87) PCT Pub. No.: WO2019/229295
PCT Pub. Date: Dec. 5, 2019

(65) Prior Publication Data
US 2021/0204815 A1 Jul. 8, 2021

(30) Foreign Application Priority Data
May 28, 2018 (FI) .................................... 20185483

(51) Int. Cl.
*A61B 5/00* (2006.01)

(52) U.S. Cl.
CPC .......... *A61B 5/0059* (2013.01); *A61B 5/6801* (2013.01); *A61B 2560/0209* (2013.01); *A61B 2560/0214* (2013.01)

(58) Field of Classification Search
CPC ... A61B 5/0059; A61B 5/6801; A61B 5/7221; A61B 5/7207; A61B 5/7217
See application file for complete search history.

(56) References Cited

U.S. PATENT DOCUMENTS 6,198,951 B1 * 3/2001 Kosuda ............... A61B 5/6826
 600/323
6,496,724 B1 * 12/2002 Levendowski ...... A61B 5/7264
 128/920

(Continued)

FOREIGN PATENT DOCUMENTS

WO 2016108056 A1 7/2016
WO 2018031570 A1 2/2018

OTHER PUBLICATIONS

European Search Report; Appl. No. 21152971.4; (dated May 25, 2021); Oura Health Oy.

*Primary Examiner* — Oommen Jacob
(74) *Attorney, Agent, or Firm* — Holland & Hart LLP

(57) ABSTRACT

The invention relates to an optical sensor system of a wearable device. The system comprises: at least two photo transmitters, a photoreceiver, receiving electronics, and a microcontroller. The microcontroller is configured to: set measurement conditions of the system; control taking at least one main sample from the received signal at one receiver channel; analyze the at least one main sample; control taking at least one test sample with at least one changed measurement condition at the same receiver channel; analyze the at least one test sample separately; compare at least one characteristic of the at least one test sample signal to the corresponding at least one characteristic of the at least one main sample signal; and change the measurement conditions to correspond to the measurement conditions used for the at least one test sample, if at least one characteristic of at least one test sample signal is better than (Continued)

corresponding at least one characteristic of the at least one main sample signal. The invention relates also to a method for controlling operation of an optical sensor system and a corresponding computer program product.

13 Claims, 6 Drawing Sheets

(56) References Cited

U.S. PATENT DOCUMENTS

| | | | |
|---|---|---|---|
| 9,215,114 B2 | 12/2015 | Emami-Neyestanak et al. | |
| 9,220,483 B2* | 12/2015 | Frankhouser | A61B 17/3476 |
| 9,307,917 B2 | 4/2016 | Hong et al. | |
| 10,595,757 B2* | 3/2020 | Lee | G01J 3/505 |
| 10,849,565 B2* | 12/2020 | Liao | A61B 5/0002 |
| 2007/0100220 A1 | 5/2007 | Baker | |
| 2010/0100004 A1* | 4/2010 | van Someren | G16H 50/30 |
| | | | 600/595 |
| 2011/0071375 A1 | 3/2011 | Baker, Jr. et al. | |
| 2011/0112379 A1* | 5/2011 | Li | G16H 50/50 |
| | | | 600/300 |
| 2011/0257697 A1* | 10/2011 | Jarverud | A61B 5/7239 |
| | | | 607/18 |
| 2012/0224891 A1* | 9/2012 | Byun | G03G 15/5058 |
| | | | 399/301 |
| 2012/0253153 A1* | 10/2012 | Trumble | A61B 5/14551 |
| | | | 600/324 |
| 2014/0275854 A1 | 9/2014 | Venkatraman et al. | |
| 2014/0376001 A1* | 12/2014 | Swanson | G02B 6/29302 |
| | | | 356/479 |
| 2015/0196257 A1 | 7/2015 | Yousefi et al. | |
| 2016/0278646 A1 | 9/2016 | Hu et al. | |
| 2016/0317096 A1 | 11/2016 | Adams et al. | |
| 2017/0360316 A1* | 12/2017 | Gu | A61B 5/7475 |
| 2018/0000424 A1* | 1/2018 | Demirtas | G16H 50/30 |
| 2018/0070839 A1 | 3/2018 | Ritscher et al. | |
| 2019/0366154 A1 | 12/2019 | Callaghan | |
| 2021/0204815 A1* | 7/2021 | Koskela | A61B 5/681 |

\* cited by examiner

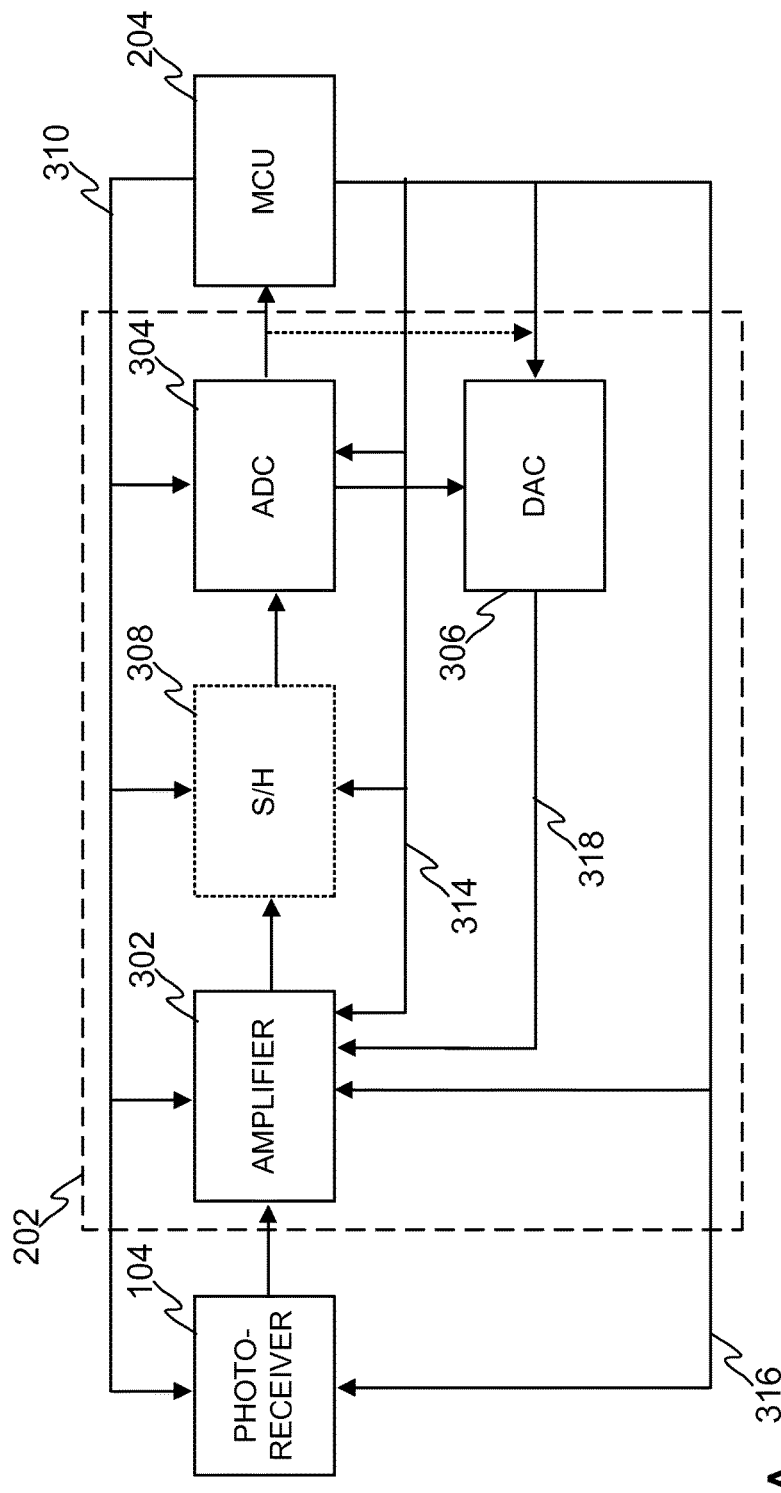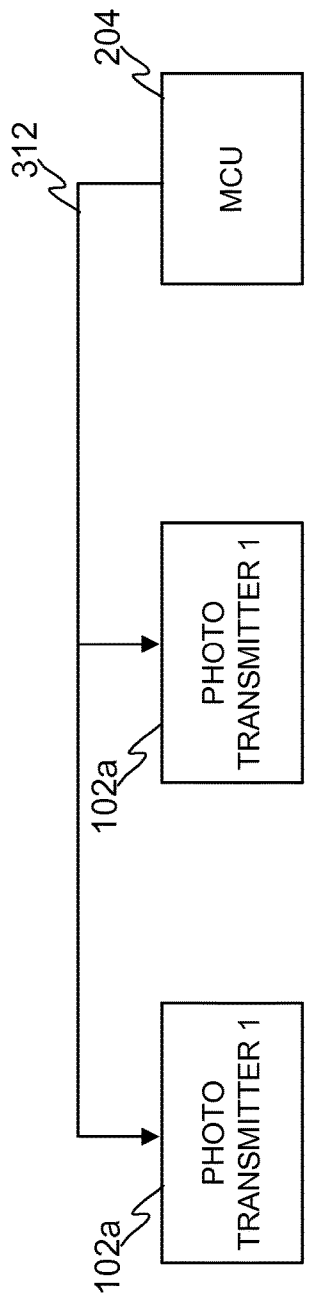
FIG. 3A
FIG. 3B

OPTICAL SENSOR SYSTEM OF A WEARABLE DEVICE, A METHOD FOR CONTROLLING OPERATION OF AN OPTICAL SENSOR SYSTEM AND CORRESPONDING COMPUTER PROGRAM PRODUCT

PRIORITY

This application is a U.S. national application of the international application number PCT/FI2019/050407 filed on May 27, 2019, which claims priority of Finnish application FI20185483 filed on May 28, 2018, the contents of all of which are incorporated herein by reference.

TECHNICAL FIELD

The invention concerns in general the technical field of wearable devices. Especially the invention concerns optical sensor system of wearable devices.

BACKGROUND

A low power consumption is a key feature for a wearable battery-operated device. An optical sensor for detecting the heart rate is one of the main power consuming functions in a wearable health monitoring or sleep monitoring device. The power consumption of the optical sensor may be optimized by pulsing the optical light source and/or optical receiver, so that measurement is done by sampling instead of measuring continuously. Between the measuring periods or pulses the transmitter and receiver can be switched off or driven to a low power mode. At the same time, other elements in the system which are connected to the transmitter and receiver may be switched off or set to a low power mode. When the measurement phase starts, all elements have to be switched on or driven to a measurement mode. It is important that all the elements are available quickly and ready almost at the same time for the successful measurement. If one element is slower than the others, all other elements must wait, and they are then consuming power in vain.

Typically, an optical biosignal detection uses a photo transmitter, e.g. a LED light source, which may be green or red or infrared. The light from the LED is directed to the skin of a person. The reflected light from the skin is then received by a photoreceiver, e.g. a phototransistor. The amplitude of the received signal indicates the blood pulses so that each heartbeat may be detected and heart rate may be defined. Using different LED colour, spectral properties of reflected light may be measured. This may improve accuracy and reliability to define heart pulses and heart rate. Furthermore, with suitable wavelengths (LED colors) other optical parameters may be measured. For example, it is possible to define oxygen saturation level, so called SpO2.

Due to the fact that biosignals are typically slow and at very low frequency band, a light source and receiver can be pulsed instead of keeping it full time ON. The heart rate is typically between 40-200 beats per minute (0.66-3.33 Hz). The heart pressure pulse is a slow changing signal typically consisting signal at 0-10 Hz frequency band. Thus, it is possible and known to pulse an optical transmitter and receiver for example at a frequency of 100-2000 Hz. Using for example 1000 Hz pulsing frequency and 50% duty cycle, the LED is kept on 0.5 ms and then switched off for the next 0.5 ms, and then switching on again for 0.5 ms and so on. In the above example the duty cycle is 50%. The duty cycle may be also less or more. For example, 10% duty cycle means that the LED in on 10% of time and off 90% of the time of one measurement cycle. In the case of 1000 Hz pulsing frequency, the LED is on 0.1 ms and off 0.9 ms. Also, it is possible to use measurement periods for measuring heart rate for example once per minute by using for example 10 seconds measuring period and then waiting 50 seconds and then measuring 10 seconds again. During the measurement period the LED and the optical receiver can be continuously on or switched as described above. During the measurement period the heart pulses are detected and the average heart rate is calculated. The rest 50 seconds is a waiting mode meaning that the LED and the optical receiver are switched off during that time period to save power.

The optical heart rate measurement is challenging due to many reasons. In some cases, multiple light sources, i.e. optical transmitters, are used. It is possible that every optical transmitter has its own photoreceiver or one optical receiver is arranged to receive light from more than one light source. It is known to switch photo receivers so that these are measured in a sequence one after another or parallel simultaneously. These are not however optimal for very low power and small wearable device.

One challenge in optical heart rate measurement relates to light interaction with the skin and body tissue. The light emitted from a photo transmitter is directed to the skin of a user. Depending on the wavelength part of light penetrates through the skin and goes to the body tissue. Depending of the tissue content (fat, muscle, blood, sweat, body liquid, etc.) and its optical properties part of the light is absorbed and part is penetrating further and part is reflected from skin and tissue. In the case of heart rate measurement as well in the case of oxygen saturation measurement it is important that some light will reach blood and interact with it. In the case of a reflective measurement a photoreceiver is arranged on the same side as a photo transmitter, the reflective part of the light interacting with skin and tissue as well blood is measured. In the case of a transmission measurement a photoreceiver is arranged on the other side body part (finger or wrist or earlobe) as a photo transmitter, the transmittance part of the light interacting with skin and tissue as well blood is measured.

In the both cases the light interacting with skin and tissue excluding blood is causing offset to a signal as this part of signal is not changing directly due to heart pulse signal. The offset may vary a lot depending on the optical system, a location and angle of photo transmitter or a location of photoreceiver related to skin and tissue, tissue content and its variation (humidity, temperature), used wavelength of the photoreceiver and spectral response of the photoreceiver.

The blood amount also varies in the area or volume on which the light is transmitted and penetrated to the skin and tissue. The amount of blood variation can be partly caused due to heart pulsation and partly due to other mechanisms such peripheral blood circulation control, body movements etc. These may cause pulse signal variation (amplitude variation), which may be good for pulse signal detection, but the pulse signal variation may cause error in detection.

The heart rate signal is primarily designed to be the signal which is based on the effect of blood absorption or reflection at the selected photo transmitter wavelength. The photoreceiver receives more or less light reflected from the blood when the heart pulse proceeds from the heart to peripheral body part. As described above the signal received by a photoreceiver is consisting different elements signal from blood, tissue and skin and varying due to many reasons. Thus, the signal offset and amplitude may vary a lot. In a typical practical situation, the signal from the optical receiver is fluctuating due to large offset variation. Also, the signal amplitude varies a lot. The problem with the large offset variation is that offset compensation cannot compensate the offset enough so that the signal is going to be out from measurement range of an analog-to-digital converter (ADC) or an amplifier of receiving electronics. This may lead to a situation to lose pulse signal as the ADC output is saturated. Another problem relates to signal pulse amplitude. If this signal amplitude is too small a reliable pulse detection cannot be done, also its time point is different to define. Too large pulse amplitude may cause a risk that signal may be out of the measurement range of ADC or amplifier and signal output will be saturated.

Heart rate measurement is playing an important role in analysis person's health and activity and sleep. Heart rate variation called heart rate variability or HRV is more advanced method to analyze heart rate data. Accurate and reliable HRV analysis needs reliable and continuous HR detection and recognition, which means that heart pulses are not missed in the measurement and detection steps. However, this is very challenging in current wearable devices with small size and low power consumption.

Typically, optical heart rate detection may be performed by an arrangement comprising a photo transmitter, photo-receiver, receiver electronics, and a microcontroller (MC). The photo transmitter is, for example, a LED which is selected to be a green, red or infrared. The photoreceiver is a phototransistor or photodiode. The receiver electronics may consist of amplifier, sample and hold circuit (S/H), analog-to-digital converter (ADC) and digital-to-analog converter (DAC). It is possible that some parts are integrated together without being clearly separated as such. Also, some parts may be realized in the different electronic means and methods such feedback loops etc. The microcontroller is anyway receiving the digitalized signal and analyzing the signal.

Prior art document WO2016108056 discloses a photoplethysmography (PPG)—based physiological sensing system employing a spatio-temporal sampling approach towards identifying and removing motion artifacts from optical signals received from a wearable optical sensing device. It multiplexes different light sources to the same receiver channel. It uses multiple light sources, so the sampling frequency has to be high. Each light source generates its own "full signal". This is technically a time multiplexed receiver with 5 different light source options.

Prior art document U.S. Pat. No. 9,307,917 discloses a method to select a right light source by a probing method to test different light sources during measuring heart rate. The light sources to be tested are measured at a higher sampling rate between the samples taken for measuring the heart rate.

Prior art document U.S. Pat. No. 9,215,114 discloses double-sampling front-end and dynamic offset modulation technique, which uses parallel sampling and amplifier receiver structures.

Any of the prior art documents does not disclose optimizing gain, offset and light source selection enabling minimum component amount, and very low power and simple system.

SUMMARY

The following presents a simplified summary in order to provide basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

An objective of the invention is to present an optical sensor system, a method, and a computer program product for controlling operation of an optical sensor system of a wearable device. Another objective of the invention is that the optical sensor system, the method, and the computer program product for controlling operation of an optical sensor system of a wearable device improves at least partly the reliability of heart rate measurement of a wearable device.

The objectives of the invention are reached by an optical sensor system, a method, and a computer program product as defined by the respective independent claims.

According to a first aspect, an optical sensor system of a wearable device is provided, wherein the system comprising: at least two photo transmitters for transmitting an optical signal, a photoreceiver for receiving an optical signal reflected from an object, receiving electronics for processing the received signal, and a microcontroller for controlling the operation of the sensor system, wherein the microcontroller is configured to: set measurement conditions of the system; control taking at least one main sample from the received signal at one receiver channel; analyze the at least one main sample for defining at least one characteristic of the at least one main sample signal; control taking at least one test sample with at least one changed measurement condition of the system at the same receiver channel; analyze the at least one test sample separately for defining at least one characteristic of the at least one test sample signal; compare the at least one characteristic of the at least one test sample signal to the corresponding at least one characteristic of the at least one main sample signal; and change the measurement conditions of the system (200) to correspond to the measurement conditions used for the at least one test sample, if at least one characteristic of at least one test sample signal is better than corresponding at least one characteristic of the at least one main sample signal.

Furthermore, the microcontroller may be configured to change the measurement conditions of the system to correspond to the measurement conditions used for the at least one test sample, if the microcontroller detects that the main sample signal is out of the measurable range or going to be out of the measurable range.

Alternatively or in addition, the microcontroller may be configured to: define optimal measurement conditions for the system based on the analyzed at least one test sample and comparison to the analyzed at least one main sample, and change the measurement conditions of the system to correspond to the defined optimal measurement conditions.

The microcontroller may further be configured to remove the at least one test sample from main sample stream and replace the removed at least one test sample by interpolating a new sample to the main signal stream.

Alternatively or in addition, the microcontroller may be configured to analyze the received signal for detecting minimum and maximum values of the received signal in a selected time window.

The microcontroller may further be configured to take the at least one test sample one to five samples after detecting the minimum and/or maximum values of the received signal.

The microcontroller may further be configured to: control taking two test samples with the same at least one changed measurement condition of the system, wherein one of the two test samples is taken close to the maximum value of the received signal and the other one of the two test samples is taken close to the minimum value of the received signal; define a heart pulse signal amplitude based on the two test sample signals; compare the defined heart pulse signal amplitude to a heart pulse signal amplitude defined from the main sample signals; and change the measurement conditions of the system to correspond to the measurement conditions used for the two test samples, if the heart pulse signal amplitude defined based on the two test sample signals is better than the corresponding heart pulse signal amplitude defined from the main sample signals.

The measurement condition of the system may be at least one of the following: gain of the receiving electronics, gain of the photoreceiver, offset of the receiving electronics, light source.

The characteristic of signal may be at least one of the following: amplitude, offset, heart pulse, heart rate.

The receiving electronics may comprise an amplifier; an analog-to-digital converter, ADC; and a digital-to-analog converter, DAC.

The main sampling frequency may be higher than the test sampling frequency.

According to a second aspect, a wearable device comprising the above optical sensor system is provided.

According to a third aspect, a method for controlling operation of an optical sensor system of a wearable device is provided, wherein the method comprising: setting measurement conditions of the system; taking at least one main sample from received signal at one receiver channel; analyzing the at least one main sample for defining at least one characteristic of the at least one main sample signal; taking at least one test sample with at least one changed measurement condition of the system at the same receiver channel; analyzing the at least one test sample separately for defining at least one characteristic of the at least one test sample signal; comparing the at least one characteristic of the at least one test sample signal to the corresponding at least one characteristic of the at least one main sample signal; and changing the measurement conditions of the system to correspond to the measurement conditions used for the at least one test sample, if at least one characteristic of at least one test sample signal is better than corresponding at least one characteristic of the at least one main sample signal.

According to a fourth aspect, a computer program product for controlling operation of an optical sensor system of a wearable device is provided, wherein the computer program product comprises program code storable on a computer readable storage medium, the program code being configured to execute the following steps when the program code is run in a microcontroller: setting measurement conditions of the system; taking at least one main sample from received signal at one receiver channel; analyzing the at least one main sample for defining at least one characteristic of the at least one main sample signal; taking at least one test sample with at least one changed measurement condition of the system at the same receiver channel; analyzing the at least one test sample separately for defining at least one characteristic of the at least one test sample signal; comparing the at least one characteristic of the at least one test sample signal to the corresponding at least one characteristic of the at least one main sample signal; and changing the measurement conditions of the system to correspond to the measurement conditions used for the at least one test sample, if at least one characteristic of at least one test sample signal is better than corresponding at least one characteristic of the at least one main sample signal.

Various exemplifying and non-limiting embodiments of the invention both as to constructions and to methods of operation, together with additional objects and advantages thereof, will be best understood from the following description of specific exemplifying and non-limiting embodiments when read in connection with the accompanying drawings.

The verbs "to comprise" and "to include" are used in this document as open limitations that neither exclude nor require the existence of unrecited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

The embodiments of the invention are illustrated by way of example, and not by way of limitation, in the figures of the accompanying drawings.

FIG. 3A illustrates schematically an example of elements of receiving electronics of an optical sensor system of a wearable device according to the invention.

FIG. 3B illustrates schematically an example of elements of transmitting electronics of an optical sensor system of a wearable device according to the invention.

DESCRIPTION OF THE EXEMPLIFYING EMBODIMENTS

Figure 1A:
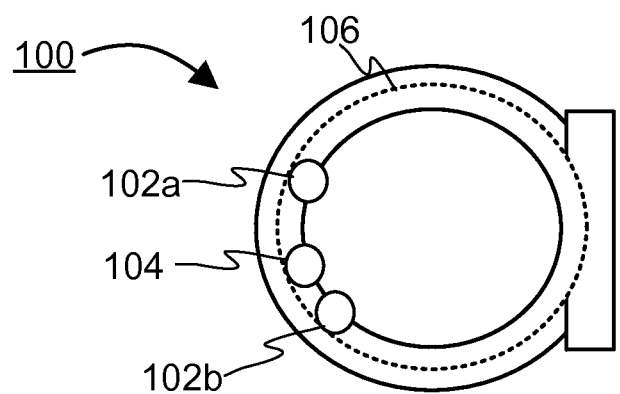
FIG. 1A illustrates schematically an example of a wearable device according to the invention.
Figure 1B:
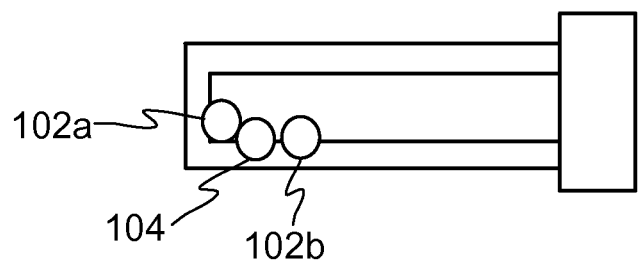
FIG. 1B illustrates schematically an example of a side view of a wearable device according to the invention.

FIG. 1A illustrates an example of a wearable device 100 according to the invention. FIG. 1B illustrates an example of a side view of the wearable device 100 according to the invention. The wearable device 100 may be a ring, a wrist device, or any other device arranged to be attached to a user's skin to measure optical properties of the skin and the tissue. The wearable device 100 may be arranged to detect heart pulses, heart rate, and/or heart rate variation, i.e. pulse to pulse time variation. The wearable device 100 may be capable for monitoring, e.g. activity, sleep, heart rate, and/or recovery of the user. In the example illustrated in FIGS. 1A and 1B, the wearable device 100 is a ring. It is preferred that a minimum number of components may be used in the photo transmitter and photoreceiver electronics, so that the components may be packaged to small volume to keep the wearable device 100 very thin and small.

Figure 2:
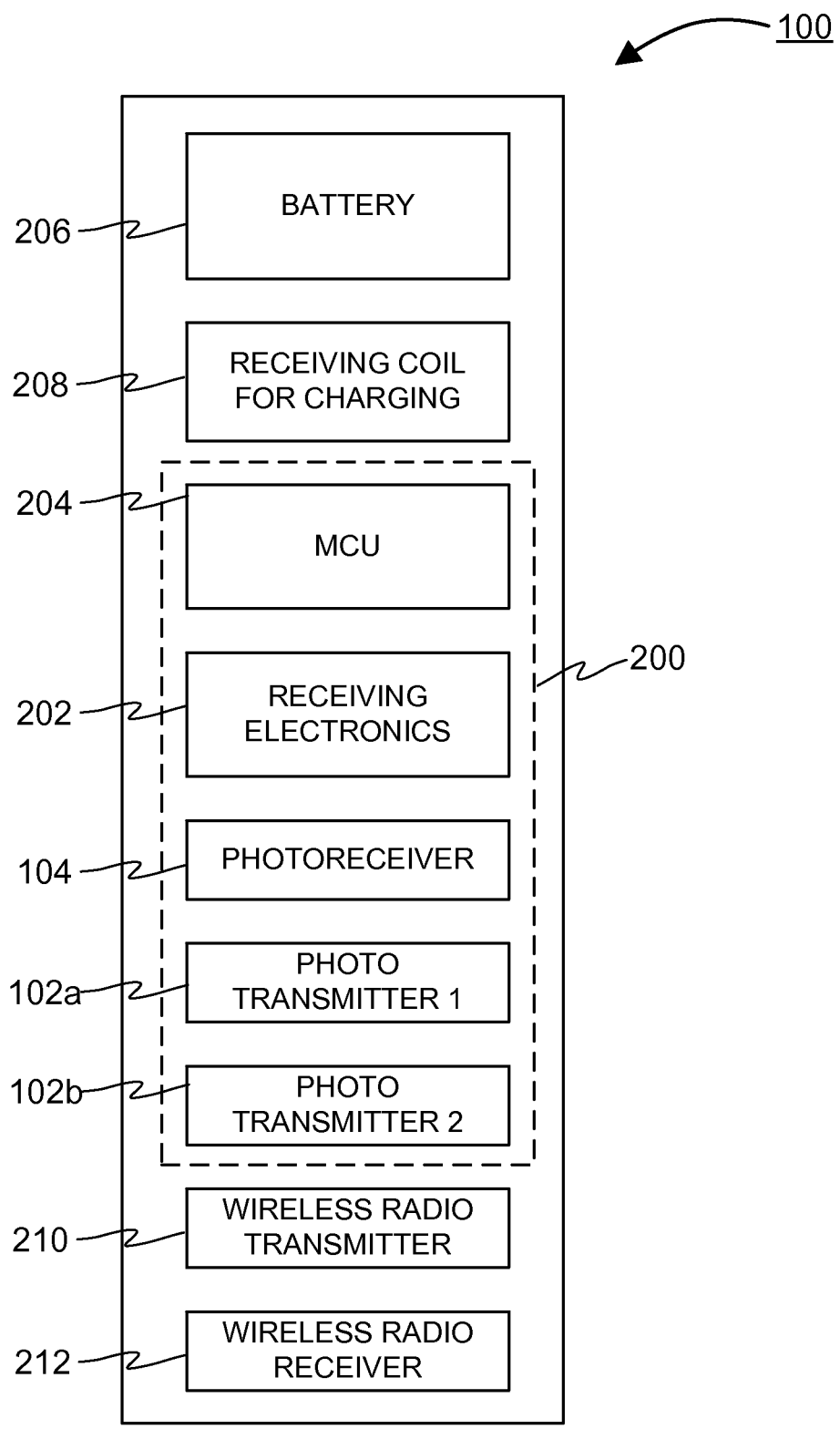
FIG. 2 illustrates schematically an example of elements of a wearable device according to the invention.

The wearable device 100 comprises an optical sensor system 200 for detecting at least one biosignal, e.g. heart rate. The optical sensor system 200 of the wearable device 100 may use a photoplethysmography (PPG) method to measure the heart rate of the user of the wearable device 100. The system 200 comprises at least two photo transmitters 102a, 102b, a photoreceiver 104, receiving electronics 202, and a microcontroller (MC) 204. FIG. 2 schematically illustrates the different elements of the wearable device 100. The elements of the wearable device 100 may be mounted to a PCB board 106 that resides along the structure of the wearable device 100 as illustrated in FIG. 1A. The wearable device 100 may further comprise an energy storage 206, e.g. a rechargeable battery, a receiving coil 208 for wireless charging, wireless communication means, e.g. one or more transmitters 210 and one or more receivers 212, for wireless communication with any other wireless devices, e.g. mobile devices, such as mobile phones or tablet computers. The wireless radio transmitter 210 may be a Bluetooth (BT) transmitter or Bluetooth Low Energy (BTLE) transmitter. The wireless radio receiver 212 may be a BT receiver or BTLE receiver. The radio communication between the wearable device 100 and other devices may be based on any known BT or BTLE protocol. Furthermore, the microcontroller 204 may comprise one or more memories, i.e. one or more computer readable storage mediums, being volatile or non-volatile for storing portions of computer program code and any information or parameters, e.g. information representing battery status of the wearable device 100 or information relating to the measurement conditions of the system 200. The microcontroller 204 may be configured to control storing of received and delivered information. The receiving coil 208 may be integrated to or embedded in the wearable device 100. The elements of the wearable device 100 may be communicatively coupled to each other.

The photo transmitters 102a, 102b may be for example LEDs, such as VSMY2940GCT-ND. The photoreceiver 104 may be a phototransistor or a photodiode, such as TEMT7000X01. The receiving electronics 202 may comprise amplifier 302, analog-to-digital circuit (ADC) 304, and a digital-to-analog circuit (DAC) 306. The ADC may comprise a sample and hold (S/H) circuit, i.e. the S/H circuit is integrated to the ADC 304. Alternatively, the receiving electronics may comprise a separate S/H circuit 308. FIG. 3A schematically illustrates the different elements of the receiving electronics together with the photoreceiver 104 and the MCU 204. According to one example, microcontroller 204, ADC 304, and DAC 306 may be integrated to be one component, i.e. a system on chip structure. The receiving electronics 202 are configured to process the received signal to digitalize the received signal for the microcontroller 204. The processing may comprise e.g. amplifying, sampling, converting, compensating, filtering etc.

The microcontroller 204 controls the operation of the sensor system 200. For example, the microcontroller 204 controls switching on and off the elements of the sensor system 200, e.g. the microcontroller may control switching on the at least two photo transmitters. In FIG. 3A the control signal(s) of the microcontroller 204 to control the switching on and off the receiving electronics 202 and the photoreceiver 104 is illustrated with the signal(s) referred with the reference sign 310. FIG. 3B schematically illustrates the control signal(s) of the microcontroller 204 to control the switching on and off the at least two photo transmitters 102a, 102b, wherein the control signal(s) is illustrated with the signal(s) referred with the reference sign 312.

One of the at least two photo transmitters 102a, 102b emits an optical signal, e.g. light, that is directed to an object (not shown in figures), i.e. the skin of the user of the wearable device 100. The photoreceiver 104 receives the signal, i.e. the light, reflected from the skin of the user. The amplitude of the received signal indicates the blood pulses so that each heartbeat may be detected from the received signal and the heart rate may be defined.

The microcontroller 204 may control measurements conditions of the system 200. For example, the microcontroller 206 may control the measurement conditions of the at least two photo transmitters 102a, 102b, the photoreceiver 104, and the receiving electronics 202. The measurement conditions of the system 200 may be at least one of the following: gain of the receiver electronics 202, gain of the photoreceiver 104, offset of the receiver electronics 202, light source. The measurement condition "light source" means the photo transmitter 102a, 102b that is used for transmitting the optical signal, i.e. light. In other words, the microcontroller 204 may control the selection of the light source, i.e. photo transmitter 102a, 102b, to be used for transmitting the optical signal, i.e. light. In FIG. 3A the control signal(s) of the microcontroller 204 to control the measurement conditions of the receiving electronics 202 and the photoreceiver 104 is illustrated with the signals referred with the reference signs 314 and 316.

As discussed in the background section the measured biometrical signal may vary widely. Therefore, the gain of the receiving electronics 202 and photoreceiver 104 and the offset of the receiving electronics 202 need to be controlled and/or changed according to variations of the received signal for keeping the received signal within the measurement range of the receiving electronics 202, e.g. ADC 304 and/or amplifier 302, and avoiding signal saturation and/or that the signal goes too small. For example, the microcontroller 204 may control the offset so that average received signal is within the measurement range of ADC 304 and amplifier 302. The offset control may be implemented in the amplifier stage, in a front stage of the ADC or in S/H circuit stage, if the sensor system comprises a separate S/H circuit 308. In FIG. 3A the control signal(s) of the microcontroller 204 to control the offset of the receiving electronics 202 is illustrated with the signals referred with the reference sign 314. Alternatively or in addition, the DAC 306 may control the offset of the amplifier 302. This is illustrated with the signal referred with the reference sign 318 in FIG. 3A. The offset control may be continuous though DAC 304 that may be configured to keep a general offset level in the middle of its measurement range.

Alternatively or in addition, the microcontroller 204 may for example control the gain so that the amplitude of received signal is large enough to enable reliable heart rate detection, but not too large so that the signal is within the measurement range of the receiving electronics 202. If the amplitude of the signal is too large, the signal output may saturate. The gain control may be implemented in the photoreceiver stage or in the amplifier stage. In FIG. 3A the control signal(s) of the microcontroller 204 to control the gain of the receiving electronics 202 or the photoreceiver 104 is illustrated with the signals referred with the reference sign 316.

Alternatively or in addition, the microcontroller 204 may for example control, which photo transmitter 102a, 102b is used to transmit the optical signal. Alternatively or in addition, the microcontroller 204 may for example control currents of the at least two photo transmitters 102a, 102b to increase or decrease the amplitude and offset of the received signal. In FIG. 3B the control signal(s) of the microcontroller 204 is illustrated with the signal(s) referred with the reference sign 312.

A low power consumption is a key feature for a wearable battery-operated device 100 and the detection of the heart rate by the optical sensor system 200 is one of the main power consuming functions in the wearable device 100. The power consumption of the optical sensor system 200 may be optimized, i.e. reduced, by pulsing the at least two photo transmitters 102a, 102b and/or the photoreceiver 104, so that measurement is performed by sampling instead of measuring continuously. Between the measuring periods or pulses, i.e. samples, the photo transmitter 102a, 102b and photoreceiver 104 may be switched off or driven to a low power mode. At the same time, other elements, e.g. receiving electronics 202, in the system 200 which are connected to the photo transmitter 102a, 102b and the photoreceiver 104 may be switched off or set to a low power mode. When the measurement phase starts, all elements of the system 200 have to be switched on or driven to a measurement mode.

Figure 4:
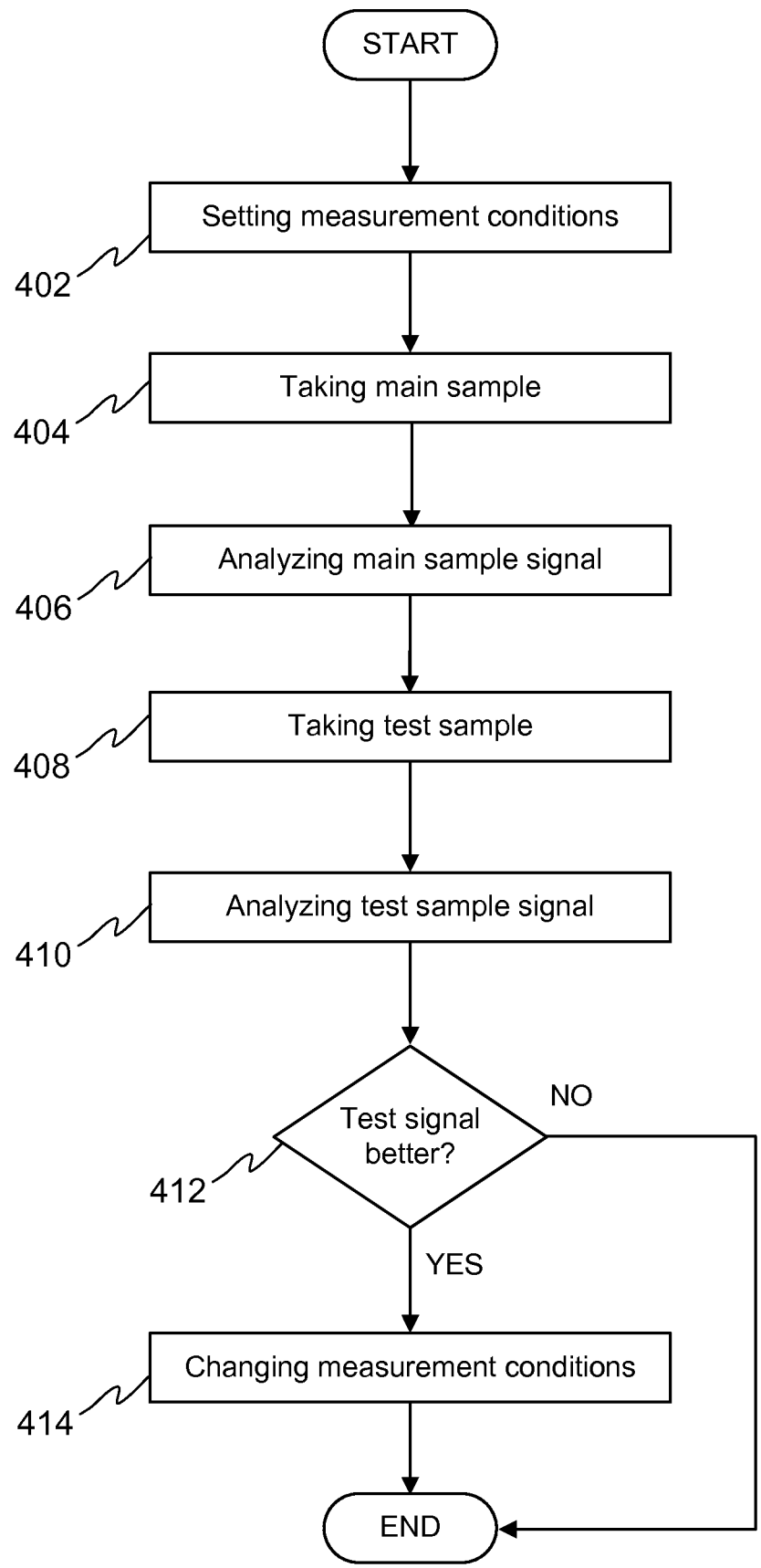
FIG. 4 illustrates schematically an example of a method according to the invention.

Next an example of a method for controlling operation of an optical sensor system 200 of a wearable device 100 according to the invention is described by referring to FIG. 4. FIG. 4 schematically illustrates the invention as a flow chart. To start the method the wearable device 100 is arranged to be attached to a user's skin, e.g. to the finger of the user, if the wearable device 100 is a ring.

When the heart rate measurement is started, the microcontroller 204 may set 402 initial measurement conditions of the system 202 that may be changed during the measurement. The initial measurement conditions may be predefined measurement conditions or based on previously used measurement conditions stored in the memory of the microcontroller 204.

The microcontroller 204 controls the sampling of the received signal at one receiver channel for taking 404 at least one main sample of the received signal. The microcontroller 204 may analyze 406 the at least one main sample for defining at least one characteristic of the at least one main sample signal. The characteristic of a signal may be at least one of the following: amplitude, offset, heart pulse, heart rate. The main sampling rate is kept constant. The main sampling frequency may be between 100 and 300 Hz. For example, if the main sampling frequency is 250 Hz, it corresponds sampling every 4 ms.

Furthermore, at least one test sample is taken 408 at certain time point(s) at the same receiver channels as the at least one main sample is taken. The at least one test sample is taken with at least one changed measurement condition of the system 200. The microcontroller 204 is configured to change at least one measurement condition of the system 200, e.g. different gain of the receiver electronics, different gain of the photoreceiver, different offset of the receiver electronics, another photo transmitter or their combination, for duration of the test sample. Preferably, the test sampling frequency is lower than the main sampling frequency, e.g. test samples may be taken 2 to 10 times per second. The test samples are taken as the main samples, but with changed measurement conditions of the system.

According to one example, the test samples may be timed to be taken at specific signal event(s), for example, when the received signal is close to its maximum and/or minimum in a selected time window, for example 0.2-1.5 seconds. The microcontroller 204 may analyze the at least one main samples for detecting the minimum and maximum values of the received signal in the selected time window. Furthermore, the microcontroller 204 may control that the at least one test sample is taken one to five samples after detecting the minimum and/or maximum values of the received signal.

The microcontroller 204 analyzes 410 the at least one test sample separately for defining at least one characteristic of the at least one test sample signal. The microcontroller 204 compares 412 at least one characteristic of the at least one test sample signal to the corresponding at least one characteristic of the at least one main sample signal. If the microcontroller 204 defines that at least one characteristic of at least one test sample signal is better than the corresponding at least one characteristic of the at least one main sample signal, the microcontroller 204 changes 414 the measurement conditions of the system to correspond to the measurement conditions used for the at least one test sample. The characteristic of the test sample signals may be defined to be better than the characteristics of the main sample signals, if the main sample signal is detected to be out of the measurable range, i.e. saturated or being too low, or detected to going to be out of the measurable range, for example a predefined distance from the limiting values of the range. After the microcontroller 204 has changed the measurement conditions of the system 200, the microcontroller 204 continues the measurement, but with the changed measurement conditions.

According to one example, two test samples may be taken with the same at least one changed measurement condition of the system 200 so that one of the two test samples may be taken close to the maximum value of the received signal and the other one of the two test samples is taken close to the minimum value of the received signal. The microcontroller 204 may define a heart pulse signal amplitude based on the two test sample signals and compare the defined heart pulse signal amplitude to a heart pulse signal amplitude defined from the main sample signals. If the heart pulse signal amplitude defined based on the two test sample signals is better than the corresponding heart pulse signal amplitude defined from the main sample signals, the microcontroller 204 changes the measurement conditions of the system 200 to correspond to the measurement conditions used for the two test samples.

According to one example, the microcontroller 204 may define optimal measurement conditions for the system 200 based on the analyzed at least one test sample and comparison to the analyzed at least one main sample. Preferably, the comparison may be provided with the main sample signals taken one to five samples after or before the at least one test sample. The microcontroller 204 may change the measurement conditions of the system 200 to correspond to the defined optimal measurement conditions of the system 200. For example, the optimal at least one measurement condition may be defined to be X % of at least one measurement condition of the test sample signal, e.g. optimal gain may be defined to be 70% of the gain of the test sample and optimal offset may be defined to be 80% of the offset of the test sample. The above example is only a non-limiting example and any other percentage values may be defined to be the optimal measurement condition value.

In addition, the measurement conditions of the test sample may be stored as an alternative measurement conditions for a situation, where the signal of the main samples with the current measurement conditions of the system 200 are going to be saturated or too low, i.e. out of measurement range of the ADC 304 and/or the amplifier 302. In that case measurement conditions of the test sample may be quickly changed to be used as the main measurement conditions of the main samples instead of the current measurement conditions of the main sample. As the test sample measurement conditions may be taken into use almost immediately, it enables that the signal may be monitored without losing any samples due to a saturation or a low signal level and furthermore the expected signal level may be known. As discussed above, the wearable device 100 is used to measure optical heart rate and heart rate variation, i.e. pulse to pulse time variation, it is important that no pulses or very few pulses are missed. Furthermore, possible tuning for the signal level may be performed with the estimated gain or offset values. Alternatively or in addition, the sensor system 200 may to keep at least one alternative measurement conditions of the system (200) always ready for a situation, when the received signal is going to be undetectable or unreliable. In the prior art systems, the new measurement conditions are started to be tested and search just when the first signal is missed causing that the system will lose some signal pulses before finding good conditions back.

Because the test samples with different measurement conditions are taken as part of series of sampling data at the same sampling frequency, the test samples are taken instead of the data samples of main sample stream. So removing test samples for analyzing purposes from the main sample stream, it may cause difficulties in the signal processing for main stream sample data. In order to avoid the difficulties in the signal processing of the main sample data, the microcontroller 204 may be configured to remove the at least one test sample from the main sample stream and replace the removed at least one test sample with a new main sample by interpolating previous and next, i.e. following, samples, for example by taking an average of them.

Figure 5:
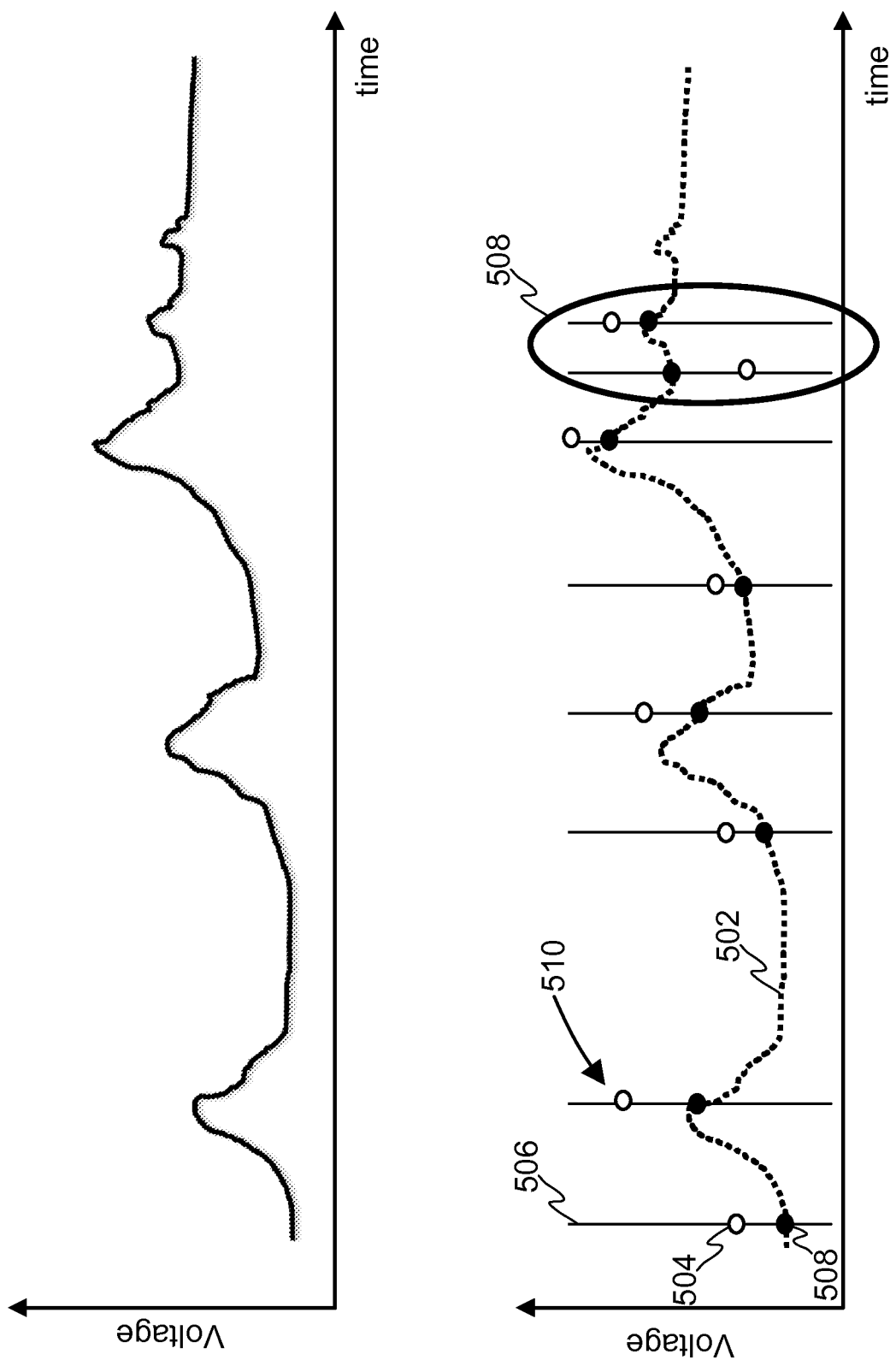
FIG. 5 illustrates an example of received signals with a method according to the invention.

FIG. 5 illustrates an example of received signals with a method according to the invention. The upper diagram illustrates the received analog signal and the lower diagram illustrates the sampled signal. The main samples are illustrated with the dashed line 502 and the test samples are illustrated with the hollow circles 504. The vertical lines 506 illustrates the test sample time points. Point 508 illustrates an example, wherein the signal of the test samples seems to be better that the signal of the main samples. Thus, at the point 506 the microcontroller is configured to change the main measurement conditions of the system to correspond the test measurement conditions. Point 510 illustrates an example, wherein the test sample time point is selected be taken when the received signal is close to its maximum. The solid black circles 508 illustrate main sample values added to main sample signal stream by interpolating previous and next samples, for example by taking an average of them, to replace the at least one test sample as discussed above.

Figure 6:
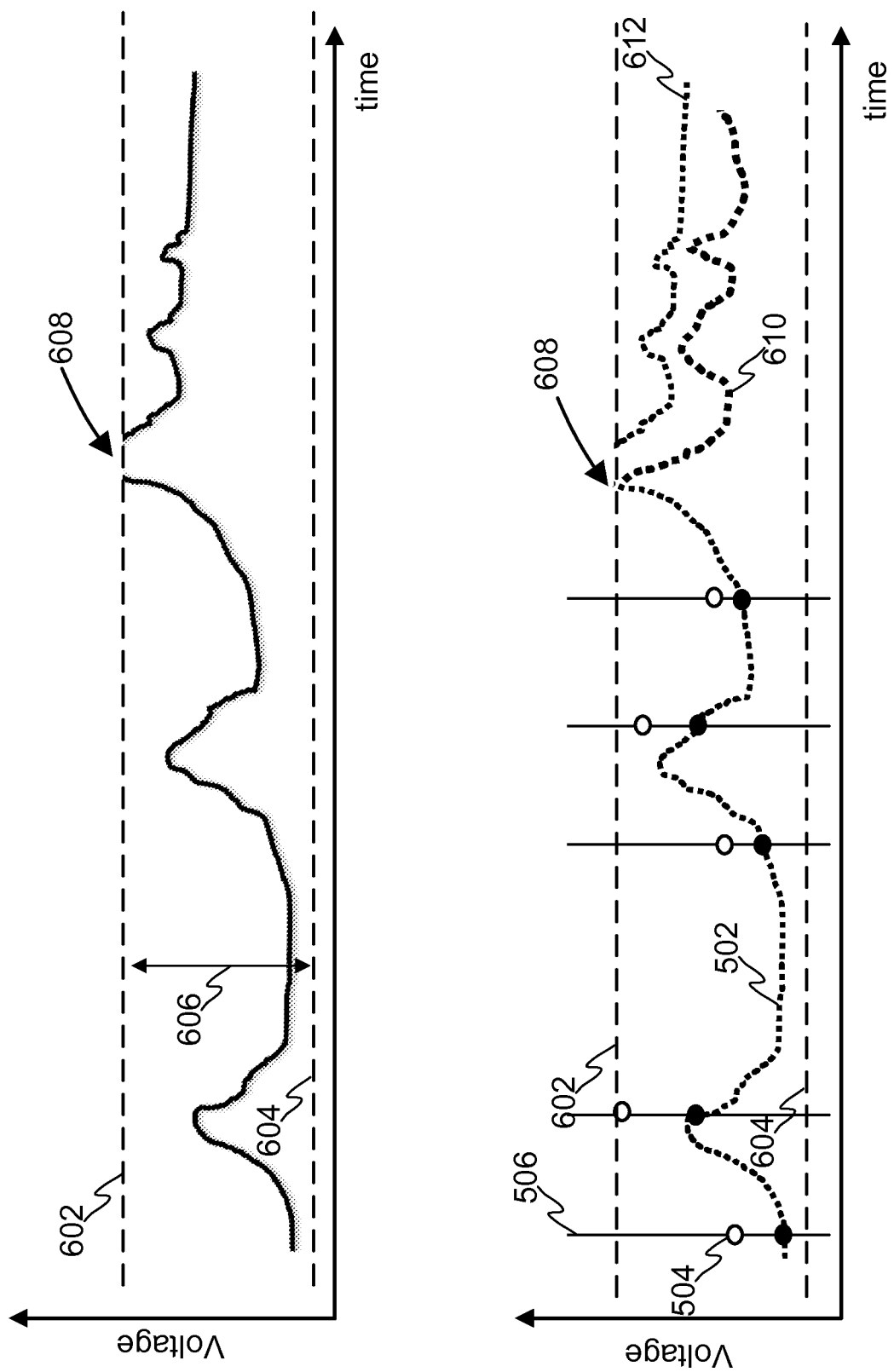
FIG. 6 illustrates another example of received signals with a method according to the invention.

FIG. 6 illustrates another example of received signals with a method according to the invention. The upper diagram illustrates the received analog signal and the lower diagram illustrates the sampled signal. The horizontal line 602 illustrates the maximum limit of the measurement range of the receiving electronics 202 and the horizontal line 604 illustrates the minimum limit of the measurement range of the receiving electronics 202. The measurement range limited by the receiving electronics 202, e.g. ADC 304 and/or amplifier 302, is illustrated by reference sign 606. At point 608 the microcontroller 204 detects that the main sample signal 502 is going to out of the measurable range, i.e. over the maximum limit of the measurement range, i.e. to be saturated. In response to the detection that the main sample signal is out of the measurable range, the microcontroller 204 is configured to change the main measurement conditions of the system 200 to correspond the test measurement conditions of a test sample signal that is within the measurement range. The dashed line 610 represents the main sample signal with the changed measurement conditions (i.e. non-saturated signal). The dashed line 612 represents the saturated main sample signal if the measurement conditions would not be changed. The change to the test measurement conditions enable that the signal may be measured without saturation and enable to measure signal changes continuously, that enables not to miss any heart pulses.

As discussed above low power consumption is important for battery operated devices. The system and the method according to the invention enable that the signal level with another measurement conditions may be followed at a lower frequency using the same channel with a minimal (low) power consumption, i.e. no additional power consumption in the measuring channel and the microcontroller 204 consumes only a bit more power. Because the system and the method according to the invention are based on one channel approach, the power consumption may be kept lower than in multiple channel approaches. Moreover, the system and method according to the invention enables that the number of the electronics may be low and no additional components are needed, e.g. additional S/H circuit or ADC, that is preferred, because the size of the wearable device 100 may be very small.

The present invention comprises an optical sensor system, a method for controlling operation of an optical sensor system and a corresponding computer program product. All these aspects of the invention comprise the same sub-features, sub-parts and sub-functionalities which are comprised in the dependent arrangement claims.

The specific examples provided in the description given above should not be construed as limiting the applicability and/or the interpretation of the appended claims. Lists and groups of examples provided in the description given above are not exhaustive unless otherwise explicitly stated.

The invention claimed is:

1. An optical sensor system of a wearable device, comprising:
   a photo transmitter configured to transmit an optical signal;
   a photoreceiver configured to receive the optical signal reflected from an object;
   receiving electronics coupled with the photoreceiver and configured to process the optical signal received by the photoreceiver; and
   a microcontroller configured to control operation of the optical sensor system, wherein the microcontroller is configured to:
      set measurement conditions of the optical sensor system;
      control taking a main sample from the optical signal, received by the photoreceiver;
      analyze the main sample for defining at least one characteristic of a main sample signal;
      change at least one measurement condition of the optical sensor system;
      control taking a test sample, from the optical signal received by the photoreceiver, with the at least one changed measurement condition of the optical sensor system;
      analyze the test sample separately for defining at least one characteristic of a test sample signal; and
      change the measurement conditions of the optical sensor system to correspond to the measurement conditions used for the test based on detecting that the main sample signal is out of a measurable voltage range of the receiving electronics or is going to be out of the measurable voltage range.

2. The optical sensor system of claim 1, wherein the microcontroller is configured to:
   define measurement conditions for the optical sensor system based on the analyzed test sample and based on a comparison between the test sample and the main sample; and
   change the measurement conditions of the optical sensor system to correspond to the defined measurement conditions.

3. The optical sensor system of claim 1, wherein the test sample is taken at a time that a second main sample is scheduled to be taken, and wherein the microcontroller is further configured to:
use, as the second main sample, a replacement sample that is based on one or more samples taken with the unchanged measurement conditions, wherein the replacement sample is used as the second main sample based on the test sample being taken at the time that the second main sample is scheduled to be taken.

4. The optical sensor system of claim 1, wherein the microcontroller is configured to:
analyze the optical signal for detecting a minimum amplitude and a maximum amplitude of the optical signal in a selected time window.

5. The optical sensor system of claim 4, wherein the microcontroller is further configured to:
take the test sample one to five samples after detecting the minimum amplitude, or maximum amplitude of the optical signal.

6. The optical sensor system of claim 4, wherein the microcontroller is further configured to:
control taking two test samples with the same at least one changed measurement condition of the optical sensor system, wherein one of the two test samples is taken within a first threshold amount of time after detecting the maximum amplitude of the optical signal and the other one of the two test samples is taken within a second threshold amount of time after detecting the minimum amplitude of the optical signal;
define a heart pulse signal amplitude based on the two test sample signals;
compare the defined heart pulse signal amplitude to a heart pulse signal amplitude defined from the main sample signal; and
change the measurement conditions of the optical sensor system to correspond to the measurement conditions used for the two test samples based on a comparison between the heart pulse signal amplitude defined based on the two test sample signals and the corresponding heart pulse signal amplitude defined from the main sample signals.

7. The optical sensor system of claim 1, wherein the measurement condition of the optical sensor system is at least one of: a gain of the receiving electronics, a gain of the photoreceiver, an offset of the receiving electronics, a light source.

8. The optical sensor system of claim 1, wherein the at least one characteristic of the main sample signal is at least one of: an amplitude, an offset, a heart pulse, a heart rate.

9. The optical sensor system of claim 1, wherein the receiving electronics comprises an amplifier, an analog-to-digital converter, and a digital-to-analog converter.

10. The optical sensor system of claim 1, wherein the receiving electronics comprises an amplifier, an analog-to-digital converter, and a digital-to-analog converter.

11. The optical sensor system of claim 1, wherein the wearable device comprises a wearable ring device.

12. A method for controlling operation of an optical sensor system of a wearable device, the method comprising:
setting measurement conditions of the optical sensor system;
taking a main sample from an optical signal received by a photoreceiver of the optical sensor system;
analyzing the main sample for defining at least one characteristic of a main sample signal;
changing at least one measurement condition of the optical sensor system;
taking a test sample, from the optical signal received by the photoreceiver, with the at least one changed measurement condition of the optical sensor system;
analyzing the test sample separately for defining at least one characteristic of a test sample signal; and
changing the measurement conditions of the optical sensor system to correspond to the measurement conditions used for the test sample based on detecting that the main sample signal is out of a measurable voltage range, or is going to be out of the measurable voltage range, of receiving electronics coupled with the photoreceiver.

13. A non-transitory computer-readable storage medium storing program code for controlling operation of an optical sensor system of a wearable device, the program code executable by a microcontroller to cause the wearable device to:
set measurement conditions of the optical sensor system;
take a main sample from an optical signal received by a photoreceiver of the optical sensor system;
analyze the main sample for defining at least one characteristic of a main sample signal;
change at least one measurement condition of the optical sensor system;
take a test sample, from the optical signal received by the photoreceiver, with the at least one changed measurement condition of the optical sensor system;
analyze the test sample separately for defining at least one characteristic of a test sample signal; and
change the measurement conditions of the optical sensor system to correspond to the measurement conditions used for the test sample based on detecting that the main sample signal is out of a measurable voltage range, or is going to be out of the measurable voltage range, of receiving electronics coupled with the photoreceiver.

* * * * *